US012558515B2

(12) United States Patent
Tsai et al.

(10) Patent No.: US 12,558,515 B2
(45) Date of Patent: Feb. 24, 2026

(54) NON-COLLAPSIBLE CATHETER TUBE

(71) Applicant: ConvaTec Technologies Inc., Las Vegas, NV (US)

(72) Inventors: Mingliang Lawrence Tsai, Holmdel, NJ (US); Pavel Zeliankevich, Chester (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 0 days.

(21) Appl. No.: 18/740,020

(22) Filed: Jun. 11, 2024

(65) Prior Publication Data

US 2024/0325686 A1 Oct. 3, 2024

Related U.S. Application Data

(63) Continuation of application No. 17/563,501, filed on Dec. 28, 2021, which is a continuation of application No. PCT/US2021/065295, filed on Dec. 28, 2021.

(Continued)

(51) Int. Cl.
*A61M 25/00* (2006.01)
*A61L 29/14* (2006.01)
*A61M 25/10* (2013.01)

(52) U.S. Cl.
CPC ....... *A61M 25/0017* (2013.01); *A61L 29/146* (2013.01); *A61M 25/005* (2013.01);
(Continued)

(58) Field of Classification Search
CPC ...... A61F 5/445; A61F 2/0022; A61F 2/0013; A61F 2002/045; A61F 2005/4455; A61F 5/442; A61F 2/04; A61F 2250/0003; A61F 5/0093; A61F 5/4405; A61F 5/44; A61F 2/0027; A61M 2210/1067; A61M 2210/1064; A61M 25/1002; A61M 25/1011; A61M 25/10185; A61M 27/00;
(Continued)

(56) References Cited

U.S. PATENT DOCUMENTS 3,866,243 A * 2/1975 Morgan ................. A42B 3/122
2/418
4,555,242 A 11/1985 Saudagar
(Continued)

FOREIGN PATENT DOCUMENTS

WO 2011136815 A1 11/2011
WO 2011139498 A1 11/2011

OTHER PUBLICATIONS

Written Opinion of International Searching Authority for PCT/US2021/065295; Dated May 18, 2022; 14 pages.
(Continued)

*Primary Examiner* — Adam Marcetich
(74) *Attorney, Agent, or Firm* — TAFT STETTINIUS HOLLISTER LLP; Ryan O. White; Derek B. Lavender

(57) ABSTRACT

An apparatus according to certain embodiments generally includes an elongated tubular member having a proximal end and an opposite distal end, and an inflatable balloon surrounding the distal end. The elongated tubular member comprises an outer tube, a non-collapsible inner tube positioned within the outer tube, and a compressible material positioned between the outer tube and the inner tube.

20 Claims, 5 Drawing Sheets

Related U.S. Application Data

(60) Provisional application No. 63/131,154, filed on Dec. 28, 2020.

(52) U.S. Cl.
CPC ................. *A61M 25/10186* (2013.11); *A61M 2025/0059* (2013.01); *A61M 2210/1067* (2013.01)

(58) Field of Classification Search
CPC .......... A61M 3/0295; A61M 25/10186; A61M 25/0017; A61M 25/04; A61M 2202/068
See application file for complete search history.

(56)                       References Cited

U.S. PATENT DOCUMENTS

| | | | |
|---|---|---|---|
| 5,308,325 | A | 5/1994 | Quinn et al. |
| 8,529,429 | B2 | 9/2013 | Goebel |
| 9,744,069 | B2 | 8/2017 | Gobel |
| 2002/0077611 | A1* | 6/2002 | von Dyck ............... A61F 5/442 604/332 |
| 2003/0220621 | A1* | 11/2003 | Arkinstall ............... A61F 5/445 604/335 |
| 2004/0222684 | A1* | 11/2004 | VanSickle ................ A47C 4/54 297/452.41 |
| 2008/0071250 | A1* | 3/2008 | Crisp ................ A61M 25/0017 604/544 |
| 2011/0040269 | A1* | 2/2011 | Cline ...................... A61F 5/445 604/335 |
| 2011/0054395 | A1* | 3/2011 | O'Dea .................. A61B 5/1076 604/97.02 |
| 2013/0079738 | A1* | 3/2013 | Hanuka ................... A61F 5/445 604/335 |
| 2014/0128974 | A1* | 5/2014 | Bromer ............... A61F 2/30721 623/14.12 |
| 2016/0279005 | A1* | 9/2016 | Crewdson .......... A61G 7/05769 |
| 2016/0279006 | A1* | 9/2016 | Crewdson ............. A61F 5/0585 |

OTHER PUBLICATIONS

International Preliminary Report on Patentability for PCT/US2021/065295; Dated Oct. 10, 2023; 7 pages.

* cited by examiner

NON-COLLAPSIBLE CATHETER TUBE

CROSS-REFERENCE TO RELATED APPLICATIONS

The present application is a continuation of U.S. patent application Ser. No. 17/563,501, filed Dec. 28, 2021, which is a continuation of International Application No. PCT/US21/65295 filed Dec. 28, 2021, and claims the benefit of U.S. Provisional Patent Application No. 63/186,546, filed 10 May 2021, and U.S. Provisional Patent Application No. 63/131,154, filed 28 Dec. 2020, the contents of each of which are incorporated by reference in their entirety.

BACKGROUND

Indwelling fecal management catheters are utilized to capture and contain liquid or semi-liquid fecal matter of non-ambulatory hospital patients in order to prevent contamination of the patient's skin by corrosive effluent, reduce the risk of contamination by potentially infectious material, and minimize soiling of the bedding. Fecal management catheters generally comprise an inflatable balloon to anchor the catheter inside the rectum, and a tube to convey the fecal matter away from the patient's rectum.

SUMMARY

In order to reduce the force exerted on the sphincter muscle during fecal management, the tubes of most indwelling fecal catheters are collapsible, which can create a leakage path for fecal matter around the outside of the catheter tube in the perianal area of a patient. Certain embodiments of the present disclosure relate to a catheter tube that may exert minimal pressure on the sphincter muscle while allowing for effective drainage of fecal matter and reduced or no leakage around the catheter tube. In some embodiments, the catheter tube comprises a material that compresses to reduce excessive pressure on surrounding tissue and accommodate patient movement. In some embodiments, the catheter comprises a soft yet non-collapsible tube that is compressible and has reduced pressure exerted to the sphincter tissue. This is in contrast to other catheter designs comprising a collapsible catheter tube (i.e., soft and collapsible) or a fixed volume air pocket that could give rise to high pressure, possibly damaging the sphincter muscle in contact of the catheter tube. Common fecal catheters employ a collapsible catheter tube as described in U.S. Pat. No. 8,016,816 B2 and EP 2,278,945 B1, while an air pocket consisting of double balloons was disclosed to provide an improved seal to rectal tissues in U.S. Pat. No. 8,939,952 and WO2007118621A1. The latter design uses a closed air pocket that has a disadvantage of an increased pressure due to the closed system of an air pocket during bowel movement, patient movement or patient sitting.

DETAILED DESCRIPTION OF ILLUSTRATIVE EMBODIMENTS

Figure 1:
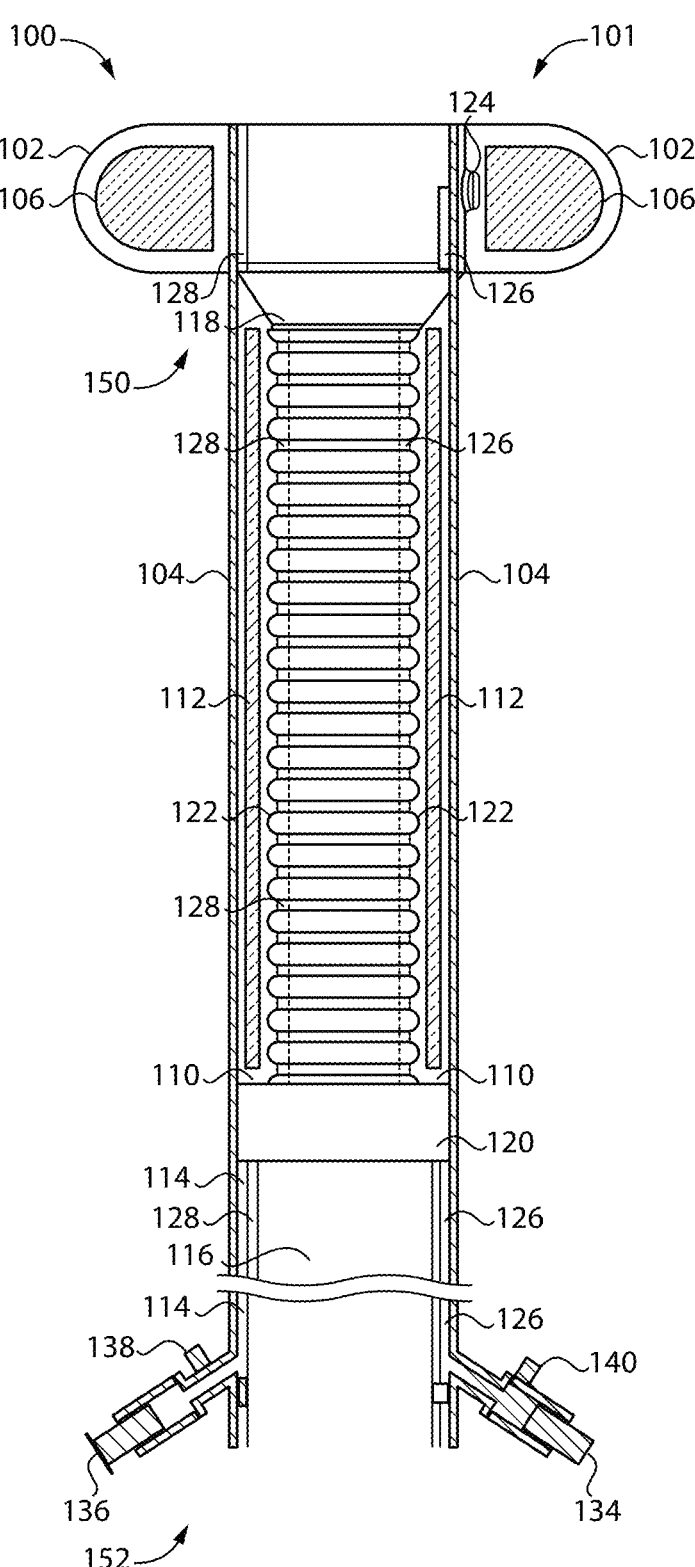
FIG. 1 is a cross-sectional illustration of an exemplary fecal management system that has a soft yet non-collapsible corrugated tube.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described.

Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Items listed in the form of "A, B, and/or C" can also mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The term "about" may be used herein to modify certain quantitative measurements. In various forms, the term "about" may signify that the expressed value may differ by up to 10%, up to 5%, or up to 1%. Thus, an indication that a pressure is "about 100 kPa" may indicate that the pressure is between 90 kPa and 110 kPa, between 95 kPa and 105 kPa, or between 99 kPa and 101 kPa.

In the drawings, some structural or method features may be shown in certain specific arrangements and/or orderings. However, it should be appreciated that such specific arrangements and/or orderings may not necessarily be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may be omitted or may be combined with other features.

In one aspect of the disclosure, provided is a medical apparatus comprising an elongated tubular element for drainage of medical waste. The medical apparatus may be part of a fecal management system (FMS), where the tubular element is designed to minimize or eliminate leakage of fecal matter around the FMS. In some embodiments, the medical apparatus comprises a compressible material positioned within the tubular element that conforms to tissue when force is exerted on the tubular element by the sphincter muscle. An exemplary medical apparatus embodied as an FMS is shown in FIG. 1.

The exemplary FMS 100 comprises a catheter 101 including an elongated tubular element 104 having a distal end 150 and a proximal end 152, and an inflatable balloon 102 surrounding the distal end 150. The main tube 104 is connected to an inner tube 122 via each of an distal adaptor 118 and a proximal adaptor 120. In the embodiment shown, the inflatable balloon 102 can be inflated with a fluid such as air or liquid (e.g., saline), for example via a port 124 connecting an inflation lumen to the main tube 104 and the chamber of the balloon 102. In some embodiments, the inflatable balloon 102 may house a compressible material 106. Formed within the elongated chamber 110 is an irrigation passage 128, a balloon inflation/deflation passage 126, and a passage 114 to the elongated tube chamber 110 for pressure management.

In the illustrated form, the device is provided as a catheter 101 of a fecal management system 100. It is also contemplated that the catheter 101 may be provided for another use, such as for use as a Foley catheter, or as another form of catheter. Moreover, it is also contemplated that the elongated tubular element 104 described herein may find use in other areas of the body, such as to form an airway for a breathing apparatus.

In the illustrated form, the distal portion of the elongated tubular element 104 is insertable into the rectum of a subject to collect bodily waste flowing from the distal portion to the proximal portion through a drainage passage 116 within the elongated tubular element 104. When the distal portion is inserted in the rectum, the inflatable balloon 102 may engage with internal body tissue to retain the distal portion within the rectum and provide a seal to divert body waste through the drainage passage 116. In certain embodiments, such as those in which the device is used as a catheter, the proximal end 152 of the catheter 101 may be connected with a waste collection device (e.g., a bag or other container) to receive waste. In other embodiments, such as those in which the device is intended for use as an airway passage, the proximal end 152 may be connected with an air source.

Figure 2:
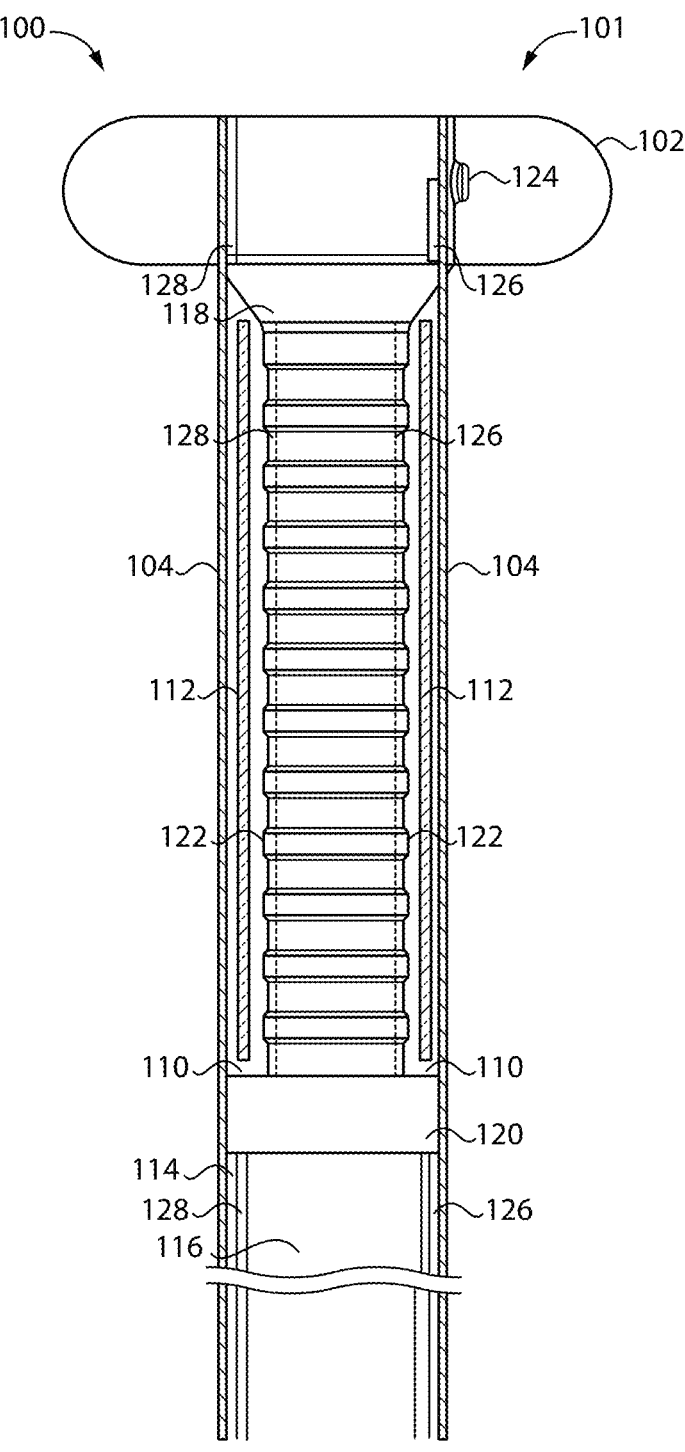
FIG. 2 is a cross-sectional illustration of an exemplary fecal management system that has a soft yet non-collapsible tube with thin sections and thick sections.
Figure 3:
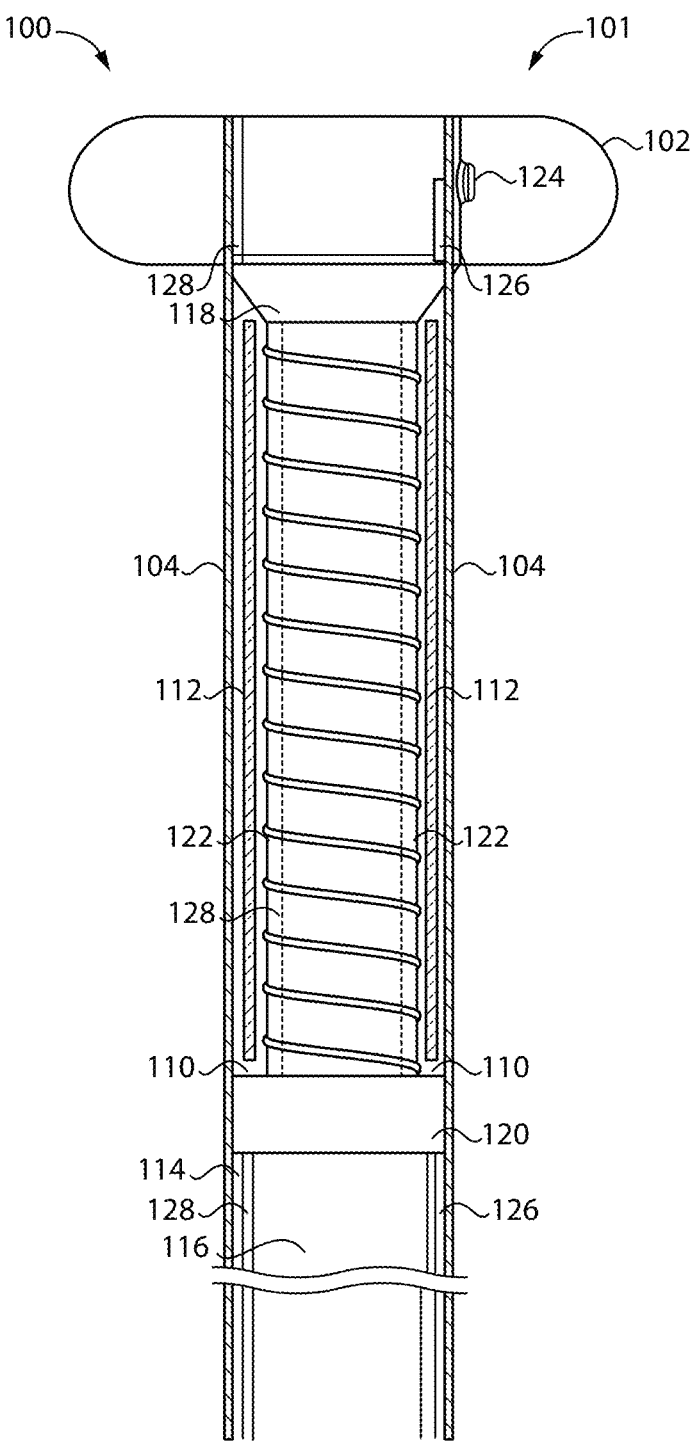
FIG. 3 is a cross-sectional illustration of an exemplary fecal management system that has a soft yet non-collapsible spiral tube.
Figure 4:
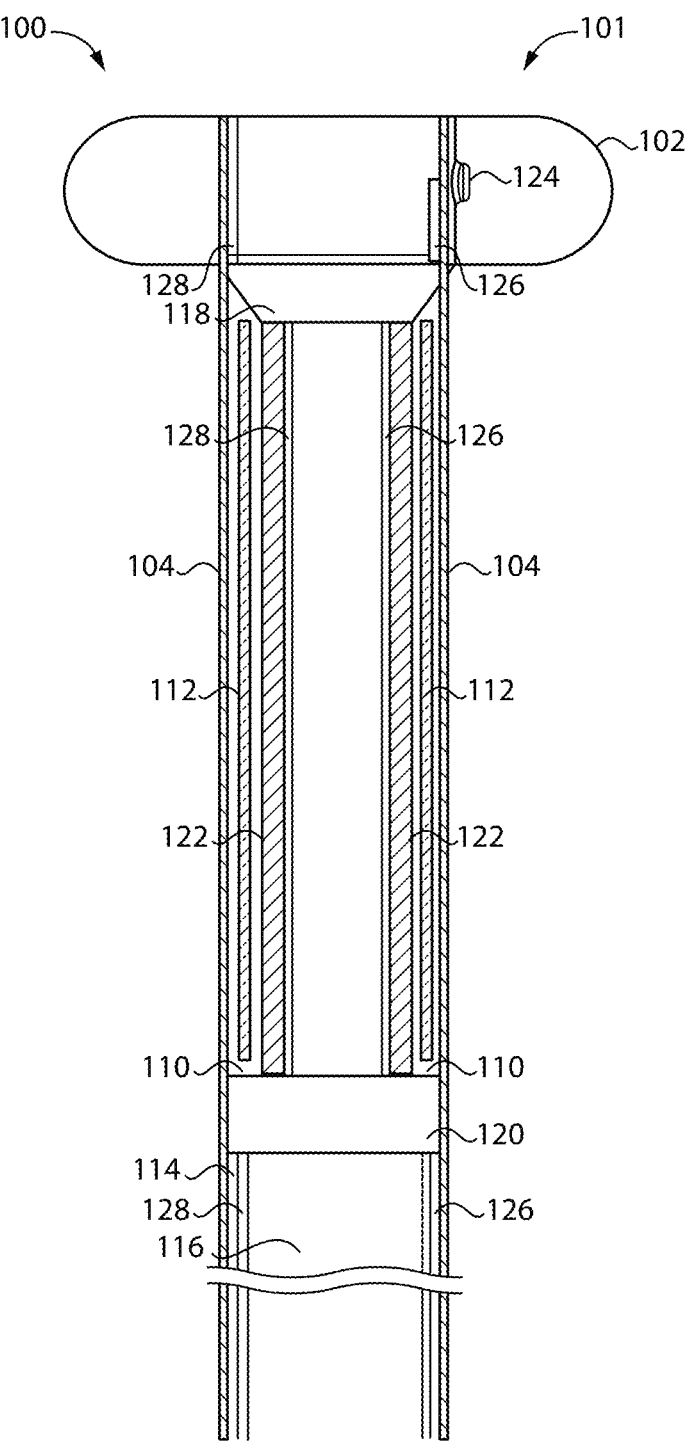
FIG. 4 is a cross-sectional illustration of an exemplary fecal management system that has a soft yet non-collapsible thicker wall tube.

In some embodiments, the elongated tubular element 104 is non-collapsible, and fluid is able to pass through the drainage passage 116 without complete obstruction. For example, the non-collapsible elongated tubular element 104 may be reinforced with wire. In some embodiments, the non-collapsible tubular element 104 comprises a spiral insert to make the tube non-collapsible. In some embodiments, the elongated tubular element 104 is further comprised of non-collapsible tubular element 122. In some embodiments, the non-collapsible tubular element 122 comprises a thick wall tube that is non-collapsible. The wall thickness may be between 0.8 mm and 4 mm, or preferably, between 1.0 mm and 2.5 mm. In some embodiments, the non-collapsible tubular element 122 comprises a corrugated tube, for example as illustrated in FIG. 1. In some embodiments, the non-collapsible tubular element 122 comprises a profile extruded tube comprised of alternating thin sections and thick sections, for example as illustrated in FIG. 2. In some embodiments, the non-collapsible tubular element 122 comprises a reinforced spiral or wire, for example as illustrated in FIG. 3. In some embodiments, the non-collapsible tubular element 122 comprises a thin wall tubing coextruded with a reinforced spiral, for example as illustrated in FIG. 3. In some embodiments, the non-collapsible tubular element 122 comprises a thick wall, for example as illustrated in FIG. 4.

The material of the elongated tubular element 104 may have a durometer of Shore A 80 (ASTM D2240) or less, or preferably not more than Shore A 70, or most preferably, not more than Shore A 60. The elongated tubular element 104 may have a wall thickness of about 0.5 mm to about 3 mm, or preferably between 0.5 mm and 1 mm. In some embodiments, the non-collapsible tubular element 122 comprises a reinforced spiral, for example as illustrated in FIG. 3. The spiral can be of the same material as the tube, or can be a different material with a higher durometer. In some embodiments, the non-collapsible tubular element 122 comprises a corrugated tube. In some embodiments, the hardness of the non-collapsible tube 122 is not more than Shore A 80 (ASTM D2240), or preferably less than Shore A 70, or more preferably not more than Shore A 60. In some embodiments, the hardness of the elongated tubular element 104 comprising a non-collapsible tube 122 and a compressible material 112 is not more than Shore A 80 (ASTM D2240), or preferably less than Shore A 70, or more preferably not more than Shore A 60.

The elongated tubular element 104 further comprises a compressible material 112 that may conform to tissue when the sphincter muscle exerts a force on the elongated tubular element 104. In some cases the compressible material 112 comprises the same material with the same properties as the compressible material 106 within the inflatable balloon 102. In some cases the compressible material 112 of the elongated tubular element 104 comprises different material and/or different properties from the compressible material 106 within the inflatable balloon 102. Non-limiting examples of materials suitable for use as compressible material 112 and/or compressible material 106 include open cell foam and polyurethane.

In some embodiments, the compressible material 106 and/or the compressible material 112 has a density (ISO 845) of about 20 kg/m³ to about 60 kg/m³, or preferably about 20 to about 30 kg/m³. In some embodiments, the compressible material 106 and/or the compressible material 112 has a compression load deflection 40% (ISO 3386-1) of about 2 kPa to about 15 kPa, or preferably 2 kPa to 5 kPa. In some embodiments, the compressible material 106 and/or the compressible material 112 has a tensile strength dry (ISO 1798) of about 50 kPa to about 200 kPa, or preferably about 100 kPa to about 150 kPa. In some embodiments, the compressible material nominal hardness (durometer, ASTM D2240) is less than 50 Shore D and/or less than 100 Shore A, or preferably less than 90 Shore A. In some embodiments, the compressible material is a fast recovery foam configured to expand up to 90% of its initial volume within 10 seconds, or preferably within 5 seconds. In some embodiments, the compressible material 106 and/or the compressible material 112 is a memory foam that keeps to the shape of the compression.

In some embodiments, the thickness of the compressible material 112 is less than about 8 mm, less than about 5 mm, or less than about 2 mm when the compressible material 112 is not compressed. In some embodiments, the thickness of the compressible material 112 is less than about 4 mm, less than about 2 mm, or less than about 1 mm when the compressible material 112 is at least about 90% of its fully compressed state.

Figure 5:
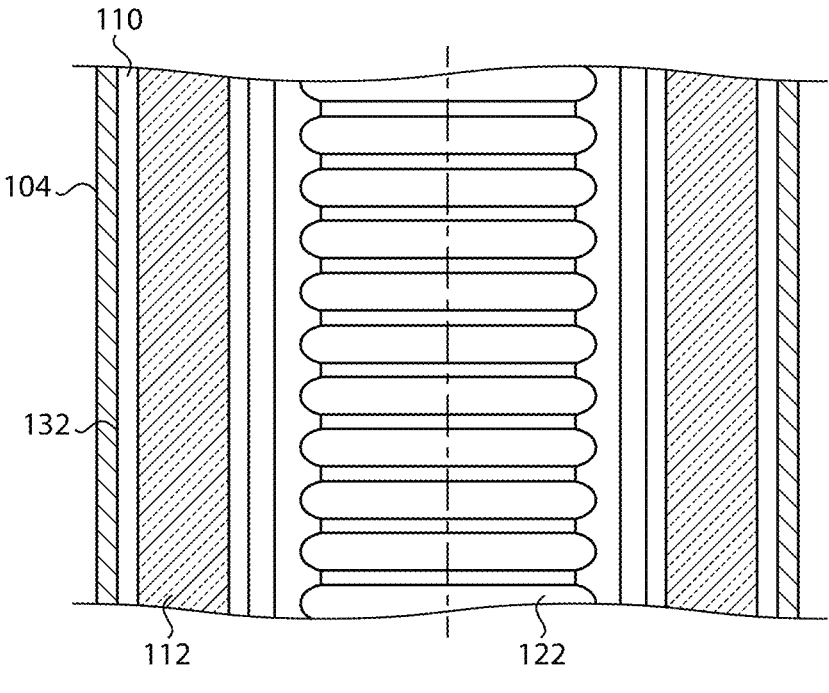
FIG. 5 is a cross-sectional illustration of an additional chamber comprising a compressible material.

The compressible material 112 is positioned within an interior of the elongated tubular element 104. In some embodiments, the compressible material 112 is positioned within a chamber 132 of the interior. As a non-limiting example, the chamber 110 may comprise a tube adjacent an interior of the elongated tubular element 104. As another example, there may be one or more chambers 132 positioned within an interior of the elongated tubular element comprising compressible material 112. The chamber 110 may be part of the interior of the elongated tubular element 104 as illustrated in FIG. 5, or may be a separate structure. In some embodiments, the chamber 110 may be defined by the interior of the outer tube 104 and the exterior of the inner tube 122. In some embodiments, the chamber 110 is comprised of polyurethane. In some embodiments, the chamber 110 is comprised of silicone. In some embodiments, the chamber 110 is comprised of a thermoplastic elastomer.

The FMS 100 further comprises a first pressure control passage 114 connecting the chamber 110 with the atmosphere through a release valve 138 and an evacuation valve system 136. The check valve system 136 is intended to allow fast inflow of fluid to the chamber 110 when forces acting upon the chamber 110 are suddenly removed. The release valve 138 is intended to release pressure when there is an increased pressure caused by urge of bowel movement or patient movement. The first passage 114 may allow for pressure equilibrium between the chamber 110 and the atmosphere through the release valve 138. When the pressure within the chamber 110 is higher than the atmosphere, the process of coming to equilibrium may involve the flow of fluid (e.g., air, liquid) from the chamber 110 through the first passage 114 to the release valve 138 to the atmosphere. For an FMS, the pressure on the sphincter tissue may be determined by the spring modulus and size of the compressible material 112 within the chamber 110.

If the chamber 110 is overfilled (e.g., compressed with a high force by the sphincter), the pressure is higher than the spring modulus is selected to bear, and the compressible material 112 is squeezed such that fluid comes out through release valve 138 under pressure. If the chamber is underfilled (e.g., as a result of sudden removal of force acting upon the chamber 110), and the expansion force of the compressible material 112 is greater than the tissue resistance, fluid will flow into the chamber 110 through the release valve 138 and/or the check valve 136, and the compressible material 112 will expand to a designated size or until tissue resistance matches the spring modulus. In some embodiments, the flow rate is proportional to the pressure gradient such that a large excess pressure in the chamber 110 results in a faster release of fluid towards the atmosphere than a smaller excess pressure.

In some embodiments the first passage 114 comprises a vent, such as release valve 138, that can facilitate the flow of fluid out of the chamber 110 in the event of sudden collapse of the tube during short permutations such as pressure from coughs, peristalsis in the bowels, or patient movement. In some embodiments, the vent comprises a micro-porous material. In some embodiments, the vent comprises a sintered polytetrafluorocthylene (PTFE). In a non-limiting example, the vent comprises Porex PM0530. In some embodiments, the vent comprises an expanded PTFE (made by Gore), having an average pore size about 200 microns to about 500 microns. The purpose of the vent is to allow the air to flow out quickly, for example, at least 0.5 liters/hr/cm$^2$ to 50 liters/hr/cm$^2$ at a pressure gradient of 70 mbar, preferably 1 liter/hr/cm$^2$ to 5 liters/hr/cm$^2$ at a pressure gradient of 70 mbar. Additional exemplary vents, partially permeable plugs, membranes, or other materials include PTFE, silicone rubber, and dense polyurethane foam. In some embodiments, the vent is a small hole or a series of holes to the atmosphere.

In some embodiments, the first passage 114 is connected to a pressure indicator that is capable of indicating pressure in the range between 5 mm Hg and 100 mm Hg, or preferably between 10 mm Hg and 50 mm Hg. The pressure indicator can be a manometer or a mechanical means to indicate a suitable pressure of the tubular chamber 110. The pressure indicator can be connected to the passage 114 through a valve 136 at the proximal end of the device. In some embodiments, the valve 136 is provided as a check valve.

In some embodiments, an FMS comprises a second passage in fluid communication with the inflatable chamber 110. In some cases a rate of fluid flow into the inflatable chamber 110 through the second passage is at least about 2-fold, 3-fold, 4-fold, 5-fold, or 10-fold the rate of fluid flow out of the inflated chamber 110 through the second passage. The faster rate into the inflated chamber 110 allows for quick filling due to bowel movement or patient movement. In some embodiments, the flow out of the inflated chamber 110 is up to about 2 ml to about 15 ml per minute. In some embodiments, the flow into the inflated chamber 110 can be up to about 20 ml, 30 ml, 40 ml, 50 ml, 60 ml, or 70 ml per minute. For an inflatable chamber 110 in an FMS, the inflatable chamber may be filled in less than about 2 minutes, less than about 90 seconds, less than about 80 seconds, less than about 70 seconds, less than about 60 seconds, less than about 50 seconds, less than about 40 seconds, or less than about 30 seconds. For an inflatable chamber 110 in an FMS, the inflatable chamber may be deflated in about 1 minute to about 15 minutes, or about 1 minute, about 2 minutes, about 3 minutes, about 4 minutes, about 5 minutes, about 5 minutes, about 6 minutes, about 7 minutes, about 8 minutes, about 9 minutes, or about 10 minutes.

Figure 6:
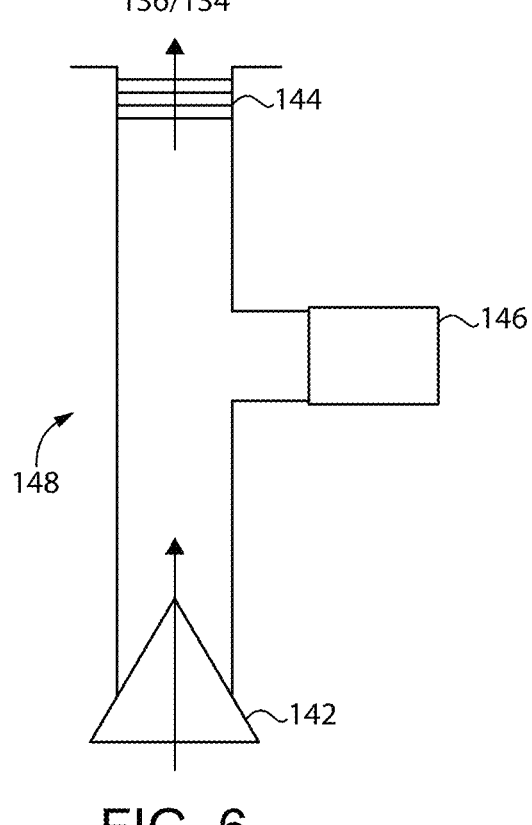
FIG. 6 shows a T-connector design with one connection to a vent and a second connection to a one-way check valve that maintains a preferred pressure differential between the elongated tubular chamber and the atmosphere.

In some embodiments, the FMS 100 comprises a third passage 126 connecting the inflatable balloon 102 to the inflatable chamber 110, and then to the same valve 134 for inflating/deflating both the balloon 102 and inflatable chamber 110. The pressure management for the retention balloon 120 through the passage 126 can be combined with the pressure management of the inflatable chamber 110 through the passage 114. In some embodiments, an additional connector can be used to control the pressure at the inflatable chamber 110 or inflatable balloon 102 as illustrated in FIG. 6. The check valve 136 is used to evacuate the fluid out of the inflatable chamber 110. Similarly, valve 134 is used to evacuate the fluid out of the inflatable balloon 102. Once the inflatable chamber 110 and the inflatable balloon 102 are deflated, the collapsed retention balloon can be inserted inside the rectum. Once the device is inserted in place, a T-connector 148 (FIG. 6) can be connected to the valve system 136 or valve system 134 through the connector 144.

The check valve 136 may be provided as a one-way valve allowing air to flow in quickly in one direction, but preventing outflow of air in the opposite direction. The release valve 138 is a vent to allow fluid (e.g., air) to be released. In some embodiments, the cracking pressure of the one-way check valve can be selected with 30 mm Hg to 35 mm Hg, or preferably 15 mm Hg to 20 mm Hg, or most preferably 5 mm Hg to 10 mm Hg. The cracking pressure will determine the pressure level of the inflatable chamber 110 or retention balloon 102. In other words, once the T-connector 148 is connected to valve system 136 or valve system 134 through the connector 144, the pressure at the inflatable chamber 110 or inflatable balloon 102 cannot exceed the cracking pressure of the one-way check valve 142.

In an exemplary method of use, the FMS 100 is prepared for insertion into the rectum by withdrawing fluid from the inflatable balloon 102 and inflatable chamber 110 using, for example, a syringe via the valve 134 and passage 126 and 114, respectively. The fluid may be withdrawn directly from the inflatable chamber 110. Withdrawal of the fluid creates a negative pressure in the inflatable chamber 110 with respect to the external atmosphere, and the surrounding atmospheric pressure collapses the inflatable chamber 110, and any compressible material 112 that may be present within the inflatable chamber 110. Once the balloon 102 is fully deflated, the distal portion of the inflatable balloon 102 and a portion of elongated tubular member 104 including an inflatable chamber 110 is inserted into the rectum, for example using a finger pocket positioned between a portion of the inflatable balloon 102 and the elongated tubular element 104. Once inserted, fluid is re-injected to allow both the inflatable balloon 102 and inflatable chamber 110 to distend. While a distended balloon 102 provides anchoring means for the catheter to stay in place, a distended chamber in the elongated tubular element allows an effective scale towards sphincter tissue, thus discouraging leaking in the perianal area. The fluid may be air or liquid. The fluid to the inflatable balloon 102 and to the inflatable chamber 110 can be the same or different. In an exemplary embodiment the fluid is air.

If the inflatable chamber 110 comprises a compressible material 112, the inflatable chamber 110 may stay distended by the action of the compressible material 106. Injecting fluid allows restoration of atmospheric fluid pressure in the inflatable chamber 110, enabling the compressible material 112 to decompress. In some cases re-injecting the same quantity of fluid as removed for insertion might generate a slight positive fluid pressure within the inflatable chamber 110. However, this positive pressure may progressively diminish as excess fluid escapes slowly to restore atmospheric fluid-pressure equilibrium. Temporary positive pressure during the bowel movement or patient movement can help to move sphincter tissue or fecal matter out of the way for proper seal. In an exemplary method of use, a T-connector 148 including a one-way check valve 142 and a release valve 146 can be coupled to the valve system 136 or 134 to maintain a system pressure that is set by the cracking pressure of the one-way check valve 142 or 146. In another exemplary method of use, a vent is connected to the inflatable chamber 110 via the passage 114 to allow the quick adjustment of the pressure in the tubular chamber 110 to create an effective seal against the sphincter tissue.

Once the inflatable balloon 102 and a portion of elongated tubular member 104 including an inflatable chamber 110 is inserted into the rectum, the non-collapsible feature of the elongated tubular element 104 including an inflatable chamber 110 and the compressible material 112 allow for drainage of fecal matter while reducing or preventing leakage around the periphery of the elongated tubular member 104. This may be achieved by attaining a pressure equilibrium between the chamber 110 and the atmosphere via the first passage 114. The inflatable chamber 110 and the compressible material 112 inside the elongated tubular element 104 are intended to balance against the compression force of sphincter muscle. For example, when the pressure of sphincter muscle is higher than the pressure of the inflatable chamber 110, the positive pressure compresses the inflated chamber 110 containing a compressible material 112 which will then trigger the pressure to be released through the release valve 138. The fluid continues to escape until the fluid pressure in the inflatable chamber 110 reaches atmospheric pressure. When the compression pressure of sphincter muscles subsides or when a patient moves, the inflatable chamber 110 expands due to the recovery of the compressible material 112, creating a negative gauge pressure. When the negative gauge pressure exceeds the cracking pressure of the check valve 136, the check valve 136 opens, allowing the fluid to flow into the chamber 110. The release valve 138 and the check valve 136 are self-adjusting and maintain the pressure balance between the inflatable chamber 110 and the surrounding sphincter muscle. The pressure on the sphincter tissue surrounding the elongated tubular element 104 comprising the compressible material 112 may be determined by the spring modulus and/or size of the compressible material 112 within the chamber 110. In some embodiments the first passage 114 in an FMS 100 comprises a vent, the process of coming to equilibrium involves the flow of fluid through the vent. In some embodiments, the first passage 114 is connected to the passage 126 designed to manage pressure control by means of an inflatable balloon 102. In some embodiments the first passage 114 is connected to the passage 126 designed to manage pressure control by means of an inflatable balloon 102 which further comprises a compressible material 106.

For an FMS having compressible material 112 within the inflatable chamber 110 of an elongated tubular element 104, the pressure on the sphincter tissue is determined by the spring modulus and/or size of the compressible material 112 within the inflatable chamber 110. If the inflatable chamber 110 is over-distended, the pressure exerted between the inflatable chamber 110 and the tissue is higher than the spring modulus of the compressible material 112 is designed to bear. In such a case, the inflatable chamber 110 is squeezed, and the fluid within the inflatable chamber 110 comes under pressure. As a result, fluid from the inflatable chamber 110 passes outwardly through the second passage to relieve the pressure. When the second passage and/or first passage comprises a vent, the vent restricts the fluid flow so that the pressure subsides slowly due to the sphincter tissue and muscle. The fluid continues to escape until the fluid pressure in the inflatable chamber 110 reaches atmospheric pressure.

If the inflatable chamber 110 is under-inflated, and the expansion pressure generated by the compressible material 112 is greater than sphincter tissue resistance, fluid will be drawn in through the first and/or second passage. As a result, the compressible material 112 will tend to expand the inflatable chamber 110 to the distended form, or until tissue resistance matches the modulus of the compressible material 112. If present, a vent may also restrict the rate of fluid in-flow.

An example system 100 may further include a pressure management device comprising a valve assembly in fluid communication with the chamber 110, which generally involves maintaining the pressure within the chamber in a selected pressure range having a minimum pressure and a maximum pressure. In certain embodiments, the minimum pressure is between atmospheric pressure and about 15 mmHg below atmospheric pressure. In certain embodiments, the minimum pressure is between 8 mmHg below atmospheric pressure and 12 mmHg below atmospheric pressure. In certain embodiments, the minimum pressure is between atmospheric pressure and about 10 mmHg below atmospheric pressure. In certain embodiments, the maximum pressure is about 30 mmHg above atmospheric pressure or less. In certain embodiments, the maximum pressure is about 20 mmHg above atmospheric pressure or less. In certain embodiments, the maximum pressure is about 10 mmHg above atmospheric pressure or less. In certain embodiments, the maximum pressure is 4-6 mmHg above atmospheric pressure. In certain embodiments, pressure management means may involve maintaining the pressure within the chamber 110 in a range of 10 mmHg below atmospheric pressure to 20 mmHg above atmospheric pressure. In certain embodiments, pressure management means may involve maintaining the pressure within the chamber 110 in a range of between 10 mmHg below atmospheric pressure to 10 mmHg above atmospheric pressure. In certain embodiments, pressure management means may involve maintaining the pressure within the chamber 110 in a range of between 10 mm Hg below atmospheric pressure to 5 mmHg above atmospheric pressure. The external pressure is a sum of the internal chamber pressure discussed above and the expansion force exerted by the resilient foam 112 onto the chamber 110, which may be about 10 mm Hg or less based on the type of foam selected according to Table 1. Therefore, at least some embodiments of the present disclosure permit a maximum cuff pressure in contact of anus sphincter with a maximum pressure of about 30 mmHg above atmospheric pressure or less, or preferably, a maximum pressure of about 20 mmHg above atmospheric pressure or less, or more preferably, a maximum pressure of about 10 mmHg above atmospheric pressure or less.

Those skilled in the art will readily appreciate that the pressure range maintained within the chamber 110 depends at least in part upon the cracking pressure selected for the check valves 136, and will readily be able to select check valves with appropriate cracking pressures to maintain a desired pressure range within the chamber 110. For example, in embodiments in which the minimum selected for the pressure within the chamber 110 is about 10 mmHg below atmospheric, the inlet check valve 136 may be selected with a cracking pressure of about 10 mmHg (e.g., 10 mmHg+/−2 mmHg). Similarly, in embodiments in which the maximum selected for the pressure within the chamber 110 is about 20 mmHg above atmospheric, the release check valve 138 may be selected with a cracking pressure of about 20 mmHg (e.g., 20 mmHg+/−4 mmHg) or less. Certain embodiments may utilize an open vent to allow for fast equilibrium to atmospheric pressure.

Certain embodiments of the present application relate to an apparatus, comprising: an elongated tubular member having a proximal end and an opposite distal end; and an inflatable balloon surrounding the distal end; wherein the elongated tubular member comprises: an outer tube; a non-collapsible inner tube positioned within the outer tube; and a compressible material positioned between the outer tube and the inner tube.

In certain embodiments, the non-collapsible inner tube is corrugated along at least a portion of a length of the non-collapsible inner tube.

In certain embodiments, the non-collapsible inner tube comprises alternating thick-walled sections and thin-walled sections.

In certain embodiments, the non-collapsible inner tube has a wall thickness between 0.8 mm and 4 mm, or between 1.0 mm and 2.5 mm.

In certain embodiments, the non-collapsible inner tube comprises a helical element.

In certain embodiments, the helical element comprises a wire.

In certain embodiments, the helical element is integrally formed with the non-collapsible inner tube.

In certain embodiments, the non-collapsible inner tube has a durometer not more than Shore A 80, not more than Shore A 70, or not more than Shore A 60.

In certain embodiments, the compressible material comprises at least one of open cell foam or polyurethane.

In certain embodiments, the compressible material has a compression load deflection 40% of about 2 kPa to about 15 kPa, or about 2 kPa to about 5 kPa.

In certain embodiments, a durometer of the compressible material is less than 50 Shore D and/or less than 100 Shore A.

In certain embodiments, the compressible material comprises a fast recovery foam configured to expand up to 90% of its initial volume within 10 seconds, or preferably within 5 seconds.

In certain embodiments, the compressible material has a tensile strength dry of about 50 kPa to about 200 kPa, or preferably about 100 kPa to 150 kPa.

In certain embodiments, the compressible material has a thickness less than about 4 mm, less than about 3 mm, or less than about 2 mm when the compressible material is not compressed.

In certain embodiments, the compressible material has a thickness of less than about 2 mm, less than about 1.5 mm, or less than about 1 mm when the compressible material is at least about 90% of a fully compressed state.

In certain embodiments, the apparatus further comprises a second compressible material positioned within the balloon.

In certain embodiments, the second compressible material is configured to move from an expanded state to a compressed state in response to a pressure compressing the balloon; and wherein the second compressible material is configured to return from the compressed state to the expanded state in response to removal of the pressure to thereby cause expansion of the balloon.

In certain embodiments, the apparatus further comprises a valve assembly in fluid communication with the chamber, the valve assembly comprising at least one pressure adjusting check valve.

In certain embodiments, the check valve comprises at least one of a duckbill valve, an umbrella valve, a disc valve, a diaphragm valve, or an open vent.

In certain embodiments, the compressible material is disposed within a chamber defined between the outer tube and the inner tube.

In certain embodiments, the apparatus further comprises a valve assembly in fluid communication with the chamber, the valve assembly comprising: a first check valve operable to allow fluid to flow out of the chamber during compression of the chamber and the compressible material; and a second check valve operable to allow fluid to flow into the chamber during expansion of the chamber and the compressible material.

Certain embodiments of the present application relate to a fecal catheter comprising the apparatus.

Certain embodiments of the present application relate to an apparatus, comprising: an elongated tubular member having a proximal end and an opposite distal end; an inflatable balloon surrounding the distal end; a first chamber formed in one of the elongated tubular member or the balloon; a first compressible material received in the first chamber; and a valve assembly in fluid communication with the first chamber, the valve assembly comprising at least one pressure adjusting check valve.

In certain embodiments, the at least one pressure adjusting check valve comprises a first check valve and a second check valve; wherein the first check valve is configured to allow fluid to flow out of the first chamber during compression of the first chamber and the first compressible material; and wherein the second check valve is configured to allow fluid to flow into the first chamber during expansion of the first chamber and the first compressible material.

In certain embodiments, the first chamber is formed in the elongated tubular member.

In certain embodiments, the elongated tubular member comprises an outer tube and an inner tube positioned within the outer tube; and wherein the first chamber is defined between the inner tube and the outer tube.

In certain embodiments, the inner tube is non-collapsible.

In certain embodiments, the first compressible material has a thickness less than about 4 mm, less than about 3 mm, or less than about 2 mm when the first compressible material is not compressed.

In certain embodiments, the first compressible material has a thickness of less than about 2 mm, less than about 1.5 mm, or less than about 1 mm when the first compressible material is at least about 90% of a fully compressed state.

In certain embodiments, the apparatus further comprises: a second chamber formed in the other of the elongated tubular member or the balloon; and a second compressible material received in the second chamber.

In certain embodiments, the first chamber and the second chamber are in fluid communication with one another.

In certain embodiments, the first compressible material is configured to move from an expanded state to a compressed state in response to a pressure compressing the first chamber; and wherein the first compressible material is configured to return from the compressed state to the expanded state in response to removal of the pressure to thereby cause expansion of the first chamber.

In certain embodiments, the check valve is configured to allow fluid to flow into the first chamber from a fluid source in response to a pressure differential between the first chamber and the fluid source exceeding a cracking pressure of the check valve.

In certain embodiments, the cracking pressure is between 10 mmHg and 25 mmHg.

In certain embodiments, the fluid source is at atmospheric pressure.

In certain embodiments, the first compressible material has a compression load deflection 40% of about 2 kPa to about 15 kPa, or about 2 kPa to about 5 kPa.

In certain embodiments, a durometer of the first compressible material is less than 50 Shore D and/or less than 100 Shore A.

In certain embodiments, the first compressible material comprises a fast recovery foam configured to expand up to 90% of its initial volume within 10 seconds, or preferably within 5 seconds.

In certain embodiments, the first compressible material has a tensile strength dry of about 50 kPa to about 200 kPa, or preferably about 100 kPa to about 150 kPa.

Certain embodiments of the present application relate to a fecal management system comprising the apparatus.

Certain embodiments of the present application relate to a method, comprising: inserting an elongated tubular member into a body cavity comprising soft tissue, wherein the elongated tubular member comprises an outer tube, a non-collapsible inner tube positioned within the outer tube, and a first compressible material positioned between the inner tube and the non-collapsible inner tube.

In certain embodiments, the method further comprises inflating a balloon coupled to an inserted end of the elongated tubular member to thereby form a seal with the soft tissue.

In certain embodiments, inflating the balloon comprises expanding a second compressible material positioned within a cavity of the balloon.

In certain embodiments, the method further comprises expanding the first compressible material from a compressed state to an expanded state, thereby forming a seal between the outer tube and the soft tissue.

In certain embodiments, expanding the first compressible material comprises introducing fluid to a chamber in which the first compressible material is received.

In certain embodiments, the body cavity is a rectal cavity.

In certain embodiments, the method further comprises: during expansion of the first compressible material, selectively flowing fluid into the first compressible material via a check valve in fluid communication with the first compressible material, thereby facilitating expansion of the first compressible material.

In certain embodiments, the method further comprises: during compression of the first compressible material, flowing fluid out of the first compressible material via a check valve in fluid communication with the first compressible material, thereby facilitating compression of the first compressible material.

In certain embodiments, the check valve is further in fluid communication with a fluid source; and wherein selectively flowing fluid into the first compressible material comprises flowing the fluid into the first compressible material only when a pressure differential between the first compressible material and the fluid source exceeds a cracking pressure of the check valve.

In certain embodiments, the fluid source is atmospheric air.

In certain embodiments, the cracking pressure is in a range of 10 mmHg to 25 mmHg.

In certain embodiments, the cracking pressure is not greater than 25 mmHg

In certain embodiments, the first compressible material surrounds the non-collapsible inner tube and is surrounded by the outer tube.

In certain embodiments, the method further comprises directing waste from the cavity to a waste collection device connected with a proximal end of the elongated tubular member via the non-collapsible inner tube.

Certain embodiments of the present application relate to an apparatus, comprising: an elongated tubular member having a proximal end and an opposite distal end; a chamber formed in the elongated tubular member; a compressible material received in the chamber; and a valve assembly in fluid communication with the chamber, the valve assembly comprising at least one pressure adjusting check valve.

In certain embodiments, the at least one pressure adjusting check valve comprises a first check valve and a second check valve; wherein the first check valve is configured to allow fluid to flow out of the chamber during compression of the chamber and the compressible material; and wherein the second check valve is configured to allow fluid to flow into the chamber during expansion of the chamber and the compressible material.

In certain embodiments, the elongated tubular member comprises an outer tube and an inner tube positioned within the outer tube; and wherein the chamber is defined between the inner tube and the outer tube.

In certain embodiments, the inner tube is non-collapsible.

In certain embodiments, the compressible material has a thickness less than about 4 mm, less than about 3 mm, or less than about 2 mm when the compressible material is not compressed.

In certain embodiments, the compressible material has a thickness of less than about 2 mm, less than about 1.5 mm, or less than about 1 mm when the compressible material is at least about 90% of a fully compressed state.

In certain embodiments, the compressible material is configured to move from an expanded state to a compressed state in response to a pressure compressing the chamber; and wherein the compressible material is configured to return from the compressed state to the expanded state in response to removal of the pressure to thereby cause expansion of the chamber.

In certain embodiments, the check valve is configured to allow fluid to flow into the chamber from a fluid source in response to a pressure differential between the chamber and the fluid source exceeding a cracking pressure of the check valve.

In certain embodiments, the cracking pressure is between 10 mmHg and 25 mmHg.

In certain embodiments, the fluid source is at atmospheric pressure.

In certain embodiments, the compressible material has a compression load deflection 40% of about 2 kPa to about 15 kPa, or about 2 kPa to about 5 kPa.

In certain embodiments, a durometer of the compressible material is less than 50 Shore D and/or less than 100 Shore A.

In certain embodiments, the compressible material comprises a fast recovery foam configured to expand up to 90% of its initial volume within 10 seconds, or preferably within 5 seconds.

In certain embodiments, the compressible material has a tensile strength dry of about 50 kPa to about 200 kPa, or preferably about 100 kPa to about 150 kPa.

Certain embodiments of the present application relate to a fecal catheter comprising the apparatus.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the inventions described herein may be employed in practicing the inventions. It is intended that the following claims define a scope of the inventions and that methods and structures within the scope of these claims and their equivalents be covered thereby.

What is claimed is:

1. An apparatus, comprising:
an elongated tubular member having a proximal end and an opposite distal end;
an inflatable balloon surrounding the distal end;
a first chamber formed in one of the elongated tubular member or the balloon;
a first compressible material received in the first chamber; and
a valve assembly in fluid communication with the first chamber, the valve assembly comprising at least one pressure adjusting check valve;
wherein the at least one pressure adjusting check valve comprises a first check valve and a second check valve;
wherein the first check valve is configured to allow fluid to flow out of the first chamber during compression of the first chamber and the first compressible material;
wherein the second check valve is configured to allow fluid to flow into the first chamber during expansion of the first chamber and the first compressible material; and
wherein the first and second check valves have cracking pressures that maintain a desired pressure within the chamber.

2. The apparatus of claim 1, wherein the first chamber is formed in the elongated tubular member.

3. The apparatus of claim 1, wherein the elongated tubular member comprises an outer tube and an inner tube positioned within the outer tube; and
wherein the first chamber is defined between the inner tube and the outer tube.

4. The apparatus of claim 3, wherein the inner tube is non-collapsible.

5. The apparatus of claim 1, wherein the first compressible material has a thickness less than about 4 mm when the first compressible material is not compressed.

6. The apparatus of claim 1, wherein the first compressible material has a thickness of less than about 2 mm when the first compressible material is at least about 90% of a fully compressed state.

7. The apparatus of claim 1, further comprising:
a second chamber formed in the other of the elongated tubular member or the balloon; and
a second compressible material received in the second chamber.

8. The apparatus of claim 7, wherein the first chamber and the second chamber are in fluid communication with one another.

9. The apparatus of claim 1, wherein the first compressible material is configured to move from an expanded state to a compressed state in response to a pressure compressing the first chamber; and
wherein the first compressible material is configured to return from the compressed state to the expanded state in response to removal of the pressure to thereby cause expansion of the first chamber.

10. The apparatus of claim 1, wherein the at least one pressure adjusting check valve is configured to allow fluid to flow into the first chamber from a fluid source in response to a pressure differential between the first chamber and the fluid source exceeding a cracking pressure of the at least one pressure adjusting check valve.

11. The apparatus of claim 10, wherein the cracking pressure is between 10 mmHg and 25 mmHg.

12. The apparatus of claim 10, wherein the fluid source is at atmospheric pressure.

13. The apparatus of claim 1, wherein the first compressible material has a compression load deflection 40% of about 2 kPa to about 15 kPa, or about 2 kPa to about 5 kPa.

14. The apparatus of claim 1, wherein a durometer of the first compressible material is less than 50 Shore D and/or less than 100 Shore A.

15. The apparatus of claim 1, wherein the first compressible material comprises a fast recovery foam configured to expand up to 90% of its initial volume within 10 seconds.

16. The apparatus of claim 1, wherein the first compressible material has a tensile strength dry of about 50 kPa to about 200 kPa.

17. A method, comprising:

inserting an elongated tubular member into a body cavity comprising soft tissue, wherein the elongated tubular member comprises an outer tube, a non-collapsible inner tube positioned within the outer tube, and a first compressible material positioned between the outer tube and the non-collapsible inner tube; and during expansion of the first compressible material, selectively flowing fluid into the first compressible material via a check valve in fluid communication with the first compressible material, thereby facilitating expansion of the first compressible material.

18. An apparatus, comprising:

an elongated tubular member having a proximal end and an opposite distal end;

a chamber formed in the elongated tubular member;

a compressible material received in the chamber; and a valve assembly in fluid communication with the chamber, the valve assembly comprising at least one pressure adjusting check valve;

wherein the at least one pressure adjusting check valve comprises a first check valve and a second check valve;

wherein the first check valve is configured to allow fluid to flow out of the chamber during compression of the chamber and the compressible material;

wherein the second check valve is configured to allow fluid to flow into the chamber during expansion of the chamber and the compressible material; and wherein the first and second check valves have cracking pressures that maintain a desired pressure within the chamber.

19. The apparatus of claim 18, wherein the elongated tubular member comprises an outer tube and an inner tube positioned within the outer tube; and wherein the chamber is defined between the inner tube and the outer tube.

20. The apparatus of claim 18, wherein the at least one pressure adjusting check valve is configured to allow fluid to flow into the chamber from a fluid source in response to a pressure differential between the chamber and the fluid source exceeding a cracking pressure of the at least one pressure adjusting check valve; and wherein the cracking pressure is between 10 mmHg and 25 mmHg and the fluid source is at atmospheric pressure.

* * * * *